United States Patent [19]

Harvey

[11] Plant 4,820

[45] Feb. 2, 1982

[54] APPLE TREE

[75] Inventor: Richard A. Harvey, Selan, Wash.

[73] Assignee: Columbia & Okanogan Nursery, Inc., Wenatchee, Wash.

[21] Appl. No.: 93,180

[22] Filed: Nov. 13, 1979

[51] Int. Cl.[3] ..... A01H 5/03
[52] U.S. Cl. ..... Plt./34
[58] Field of Search ..... Plt./34

*Primary Examiner*—Robert E. Bagwill

*Attorney, Agent, or Firm*—Christensen, O'Connor, Johnson & Kindness

[57] ABSTRACT

An early ripening yellow-green apple with uniformly round form and a smooth skin, the fruit having a high total solids and acid level making for excellent keeping qualities. The leaves of the new tree resemble those of standard Red Delicious while the color of the skin of the fruit is slightly greener than that of standard Golden Delicious.

4 Drawing Figures

BACKGROUND

This discovery relates to a new and distinct early ripening variety of apple tree having yellowish-green, smooth skinned fruit high in total solids and acid level, and that was discovered growing in a planting of standard Golden Delicious seedlings in the discoverer's orchard on Barrett Road, Selah, Wash., U.S.A. The new variety, also grown in Columbia and Okanogan Nursery Orchards, East Wenatchee near Rocky Reach Dam, has been reproduced successively through third generation trees by budding and grafting. The tree was discovered as a natural bud mutation standing out as distinctive from its parent Golden Delicious tree.

DRAWINGS

Identifying characteristics of the new tree are depicted in the accompanying photographic prints in which:

FIG. 1 shows a representative group of branches bearing mature fruit;

FIG. 2 shows a representative leaf;

FIG. 3 shows a representative mature apple; and,

FIG. 4 shows the cut face of a halved apple of the new variety.

DETAILED DESCRIPTION

Fruit: Fruit of this new variety is a yellowish-green (No. 234, Barium Yellow, Plate XVI, "Color Standards and Color Nomenclature" by Robert Ridgway), with submerged or indistinct greenish lenticels, medium hard, variable in size (i.e., 2½ to 3 inches in axial diameter), quite uniformly of oblong unsymmetrical form, with rounded ventral surface and flaring circular cavity approximately ½ inch deep and ½ inch wide. The fruit ripens about the same time as Yellow Transparent and Lodi, namely about August 1st in the Yakima/Selah/-Wenatchee, Wash. region. The apples are also cuneate and rounded at the base, and rounded to truncated at the apex, with a stem length of approximately 1 inch and of medium thickness. The skin is smooth and of medium thickness and toughness and the flesh is creamy white, with the surface of the pit cavity colored between white and yellow. High in total solids, the flesh texture is firm with few fibers, fairly even ripening, an acid flavor and a distinctive aroma, making a good eating apple and also a good cooking apple with medium keeping qualities and medium resistance to insects and diseases. Ability to withstand handling and shipping is also medium. High in acid content, fruit of the new variety has a storage life at least three times that of Yellow Transparent. Its sugar/acid balance makes it a good eating and cooking apple.

Flowers: The new variety comes into blossom approximately by April 28 in the East Wenatchee area and into full bloom approximately by May 5 in that area, medium for apple trees generally in the area. The flowers are medium large and pink in color.

Leaves: The leaves of the new variety are abruptly pointed, medium thick, of generally ovate form and of medium size (i.e., length approximately 4 to 4½ inches and width approximately 1½ to 2 inches). The leaves are of dark green color and of rugose texture with finely serrated margins and a crenate marginal character. The petioles are of medium length and of medium thickness.

Trunk, Branches, Lenticels: The trunk of the new variety is medium in structure (between stocky and slender) with medium rough bark texture. The branches are also medium in structure and of medium smoothness, with a grayish surface running to green, but not glossy nor dull. The lenticels are small in size and medium in number. Bark color and appearance generally resemble Golden Delicious.

Tree: The tree of this new variety is of medium size and medium in its degree of vigor of growth. In form, it is dense, upright and round topped. It is a hardy, very self-fertilizing, productive and regular bearer.

I claim:

1. A new and distinct variety of early ripening apple tree with yellowish-green, smooth-skinned fruit of medium size as compared with Golden Delicious and Yellow Transparent, a relatively high total solids and acid content, medium size and uniform roundish-conical shape, as shown and described.

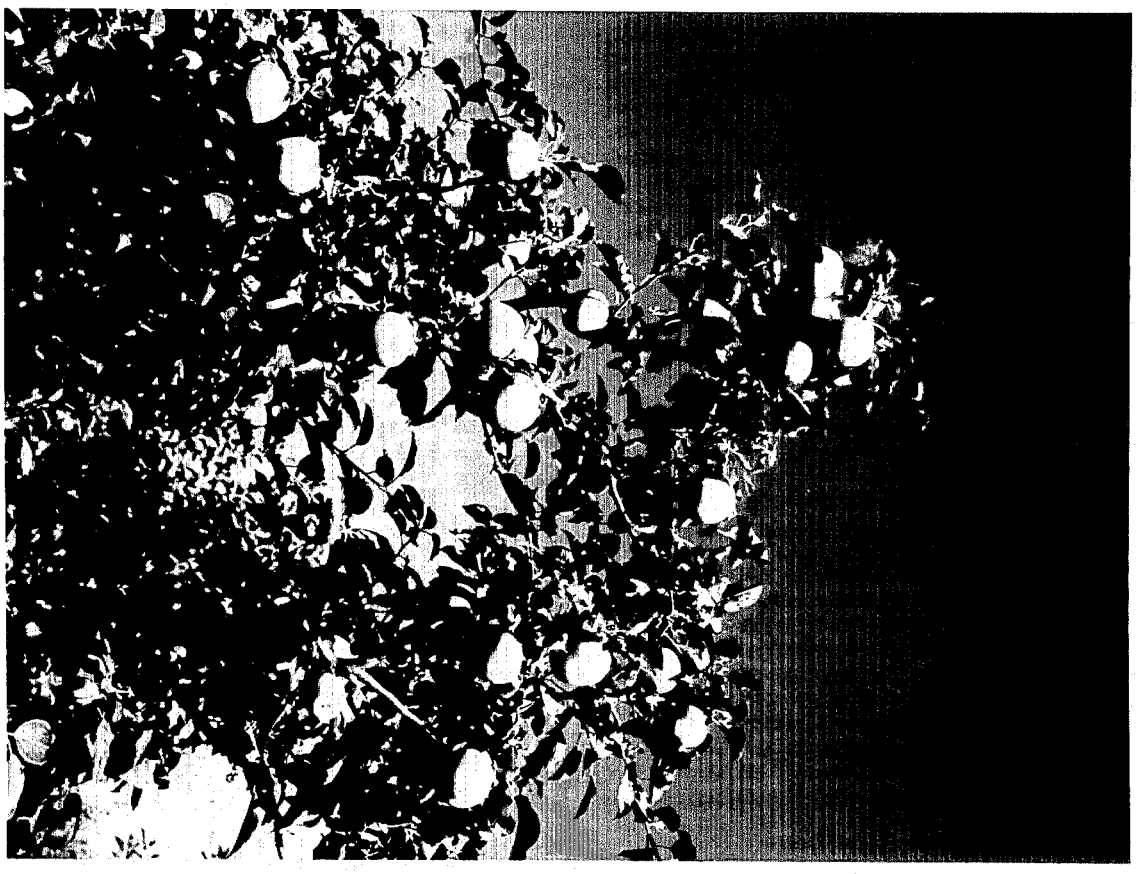
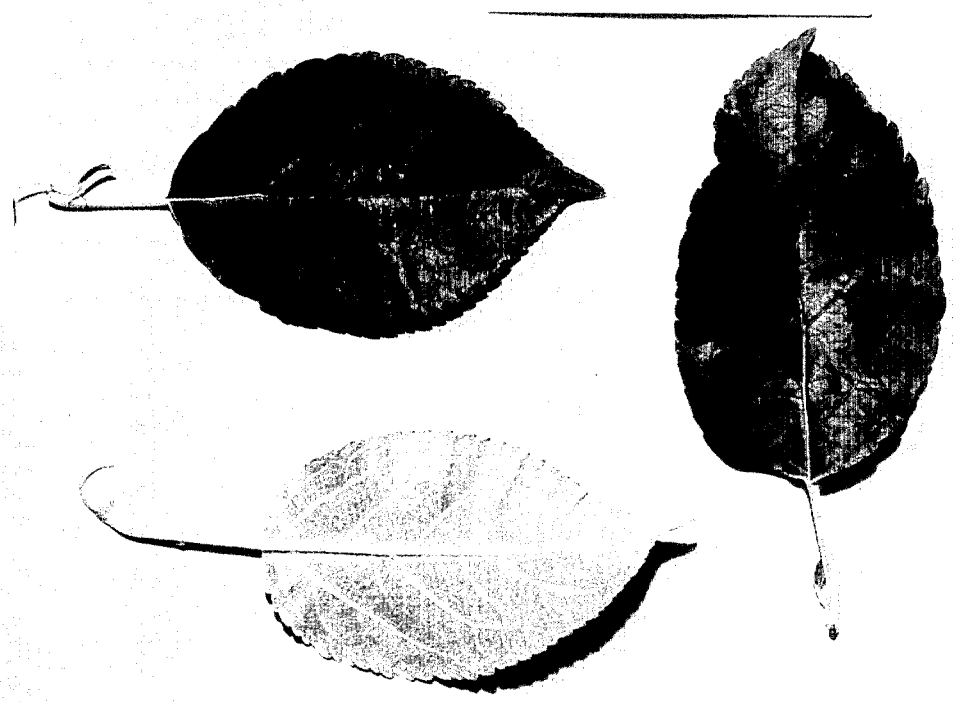

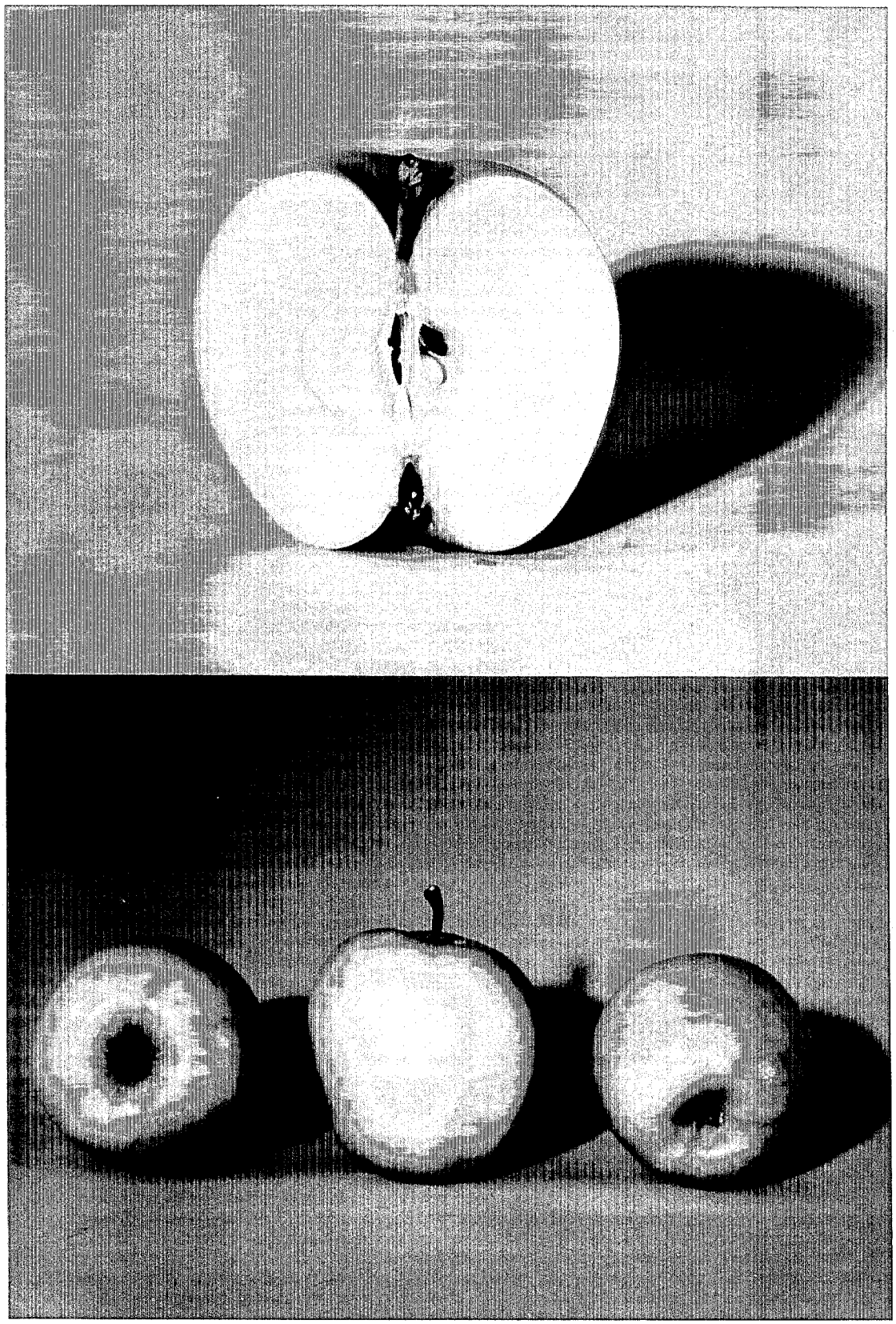

* * * * *